United States Patent [19]

Striebel

[11] Patent Number: 5,392,794
[45] Date of Patent: Feb. 28, 1995

[54] DENTAL FLOSS FOR BRACE WEARERS AND THE LIKE

[76] Inventor: John S. Striebel, 10319 Yellow Locust La., Spring Valley, Ohio 45370

[21] Appl. No.: 154,298

[22] Filed: Nov. 18, 1993

[51] Int. Cl.⁶ ............................................. A61C 15/00
[52] U.S. Cl. ..................................... 132/324; 132/321
[58] Field of Search ............... 132/321, 323, 324, 325, 132/329

[56] References Cited

U.S. PATENT DOCUMENTS

| | | | |
|---|---|---|---|
| 2,612,177 | 9/1952 | Footer | 132/324 |
| 4,133,339 | 1/1979 | Naslund | 132/323 |
| 4,807,752 | 2/1989 | Chodorow | 132/323 |
| 5,094,255 | 3/1992 | Ringle | 132/321 |

*Primary Examiner*—John G. Weiss
*Attorney, Agent, or Firm*—Randall S. Wayland

[57] ABSTRACT

A threadable dental floss (20) is shown in FIG. 3A for cleaning of a user's teeth when said user is wearing braces, bridgework, or the like. The threadable dental floss (20) includes a strand having a first end (26) and second end (26') and a semi-rigid threader (24 and 24') including a curvature formed substantially along its whole length (L'), integrally bonded to and attached to the strand member (22). The semi-rigid threader (24) preferably is made from low friction plastic in an injection molding process. Preferably, multiple sections of the threadable floss are interconnected in a chain-like fashion and are unwound from a dispenser including a spool (FIG. 3B). The user, without having to cut the strand (22), can separate a ready-to-use section of threadable floss (20) with an included curved threader section by simply exerting a small tensile force (2 pounds or less) on the floss chain. This will disconnect a threadable floss section (20) from the next adjacent floss section at the quick disconnect section (42) (FIG. 3C). The present invention provides a convenient, low cost, and efficient threadable floss for brace wearers and the like.

19 Claims, 4 Drawing Sheets

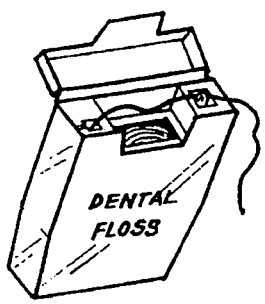
Fig. 1 "Prior Art"
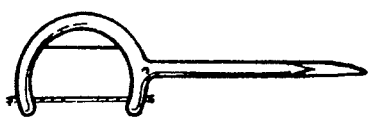
Fig. 2A "Prior Art"
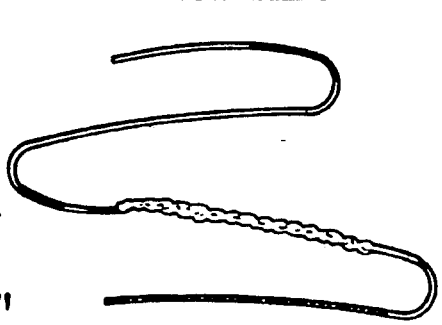
Fig. 2C "Prior Art"
Fig. 2B "Prior Art"
Fig. 2D
Fig. 2E
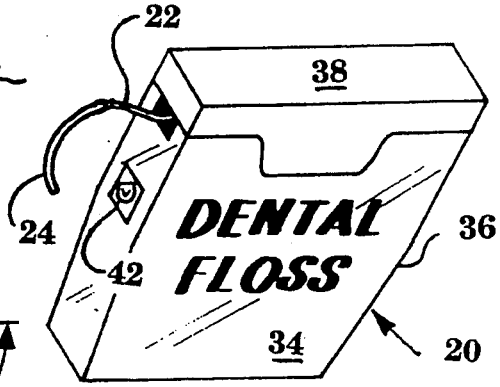
Fig. 3B
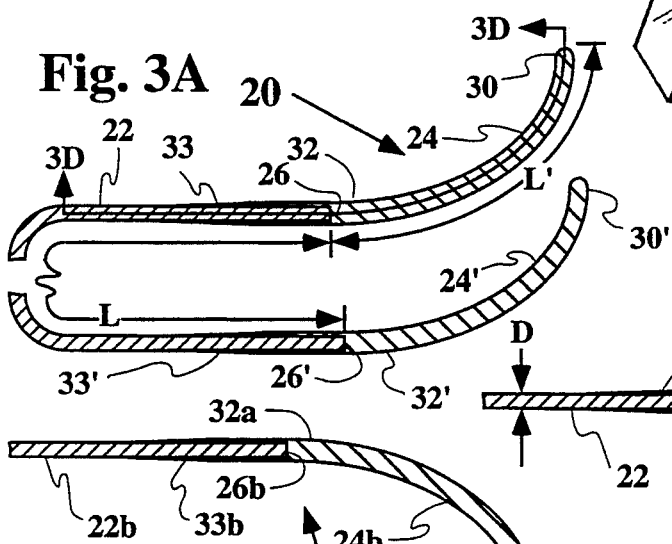
Fig. 3A
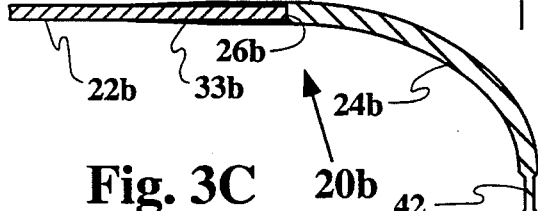
Fig. 3D
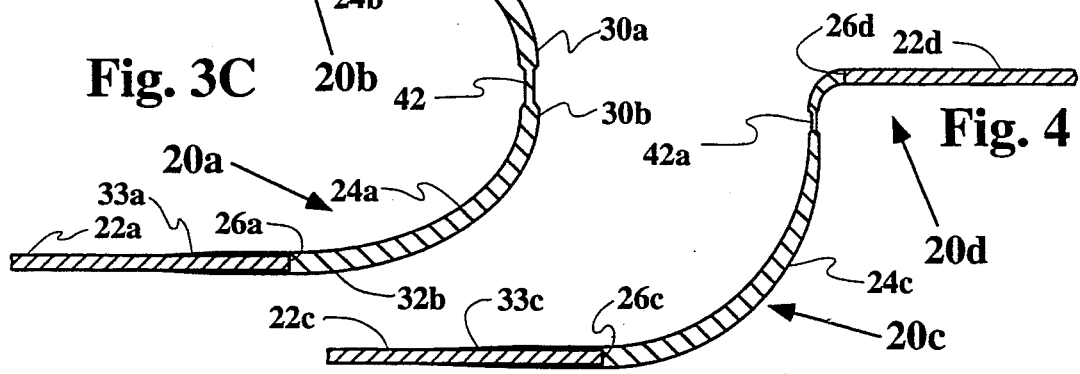
Fig. 3C
Fig. 4

DENTAL FLOSS FOR BRACE WEARERS AND THE LIKE

FIELD OF THE INVENTION

The invention relates to the area of devices used in improving dental hygiene and, more specifically, to the area of dental floss for flossing between the interproximal spaces between a person's teeth.

BACKGROUND OF THE INVENTION

In the area of dental floss, various floss implements have been developed to aid in flossing the interproximal spaces between a person's adjacent teeth. Most everyone, at one time or another, has used a dental floss as shown in FIG. 1 which is contained within a dispenser unit and includes waxed, unwaxed, or even mint flavored floss. The floss is held between the user's hands and inserted between the user's teeth to aid in removing deposits of bacterial plaque (tartar) and the like. Bacterial plaque generates acids which attack the teeth and gums, resulting in tooth decay, tender and bleeding gums, and foul smelling breath. The floss is typically moved in a sawing action between the interproximal spaces between adjacent teeth to remove debris such as food stuffs and tartar which have the tendency of building up or getting caught between the user's teeth. Removal of such deposits and tartar is essential to proper dental hygiene and can greatly reduce, if not eliminate, dental disease. The most common type of floss is contained on a spool within the aforementioned dispenser and includes a stamped metal cutting edge for removing the floss from the spool after a predetermined amount of floss has been stripped out by the user.

Improvements on the basic dental floss described above have been made, such as placing a short floss section in a holder as shown in FIG. 2A. The holder as shown in FIG. 2A is grasped by the user and used in a sawing action to remove deposits between the user's teeth. A pick is formed on one end and is used for removing larger deposits, somewhat like a tooth pick. This type of floss makes flossing easier for those who lack dexterity. Unfortunately, although both of these floss types work well for their intended applications, they can't be used by persons wearing braces or who have bridgework because the floss needs to be inserted underneath the brace or bridge in some manner. The first type can't be threaded between the user's teeth because it is simply too limp. The second can't be placed between the user's teeth because the floss section is connected to the frame at both ends.

In an attempt to solve this problem and provide a floss that can be used for brace wearers and persons with bridgework, Flossaid Corp. of San Jose, Calif., has developed the BRIDGEAID dental floss threader for guiding dental floss under bridgework and braces. U.S. Pat. No. 4,133,339 to Naslund describes this floss threading device. The device includes a deformable eye such that the eye can compress when being threaded through the interproximal spaces between the user's teeth. Although this device works adequately, it is inconvenient because the floss needs to be threaded through each dental floss threader, individually, each and every time the user wishes to floss. Furthermore, since the floss essentially has to be doubled over during this threading operation, the floss is difficult to thread through the tighter spaces between the user's teeth, i.e., because of the doubled thickness of the floss.

Oral-B Laboratories of Redwood City, Calif., has attempted to solve the same problem in a different fashion. Oral-B has developed the SUPER FLOSS dental floss, which is a flossing product which includes a short threading section and a spongy flossing section. U.S. Pat. No. 4,008,727 to Thornton describes this type of dental floss. The floss includes a section which is coated with a hardened coating which stiffens the floss slightly. It is thought that this section aids in threading the floss under braces and the like. However, the coated threading section on this device does not exhibit enough rigidity to be easily placed between the user's teeth, i.e., it is still too limp. Furthermore, it is difficult to grasp when it is wet with saliva because of its small size and lack of rigidity. Indeed, it is also difficult to find after being inserted between the user's teeth because of its small size.

In another device, which is described in U.S. Pat. No. 3,930,059 to Wells, a method of forming a continuous arrangement of dental floss articles is described. The floss device includes spaced apart sections which are coated with wax or plastic to provide a semi-rigid section which can be used as a threader. The sections of floss are dispensable from a spool contained within a dispensing container. The floss sections are cut off at the tip of the stiffened section to form a usable section. However, these devices have the disadvantage that the threaders are straight such that when the threader is inserted into the mouth, the threader has the tendency to contact the roof of the mouth. Furthermore, the device is not in a position where it can be easily grasped by the user because of the angle of insertion. Also, it is difficult to thread between the user's back teeth because of the lack of a curvature. Finally, although more convenient than individually threading each threader, the device still needs to be cut from a spool at a quite precise location.

SUMMARY OF THE INVENTION

In light of the benefits and inadequacies of the prior art dental flosses, the present invention is a threadable dental floss including a semi-rigid threader integrally attached to, and bonded to, a strand for use in flossing by brace wearers and the like. The low friction threader element allows the user to thread the floss under braces and bridgework with minimal effort. Further, the threader preferably includes a curved section on the threader such that the inner roof of the mouth is not contacted during insertion. Furthermore, the threader is easily grasped once inserted, and it is easier to thread between the user's back teeth. A further aspect of the invention includes interconnecting the adjacent floss sections with a quick release section. This quick release section allows the floss sections to be removed from each other and from a dispenser spool with ease. This quick release section has eliminated the need to cut the floss as required in the prior art. Various methods of providing a quick release section for interconnecting the floss sections in a chain-like fashion are provided.

The present invention solves a long-felt need of having an easily dispensable, quick-releasing dental floss for brace wearers and the like which includes a semi-rigid threader section integrally bonded and attached to the floss thread section, which preferably includes a curvature formed substantially along its length and which is easily threaded between the user's teeth and can be readily manufactured in a mass production environment.

It is a feature of the present invention to provide a dental floss, comprising a strand having a first end, a second end, a diameter (D), and a length (L) in between said first and second ends, said length (L) is useful for passing between an interproximal space between a user's adjacent teeth to remove deposits, a threader which is semi-rigid having a tip on one end, a trailing end on the other, a length (L') and a curvature formed substantially along the length (L'), said trailing end being integrally attached to, and bonded to, said strand at one of said first end and second end of said strand, said threader providing a semi-rigid starter section for threading said strand through said interproximal space between said user's adjacent teeth.

It is another feature of the present invention to provide a dental floss chain, comprising a plurality of interconnected dental floss sections, each dental floss section including a strand having a first end and a second end, a diameter (D), and a length (L) in between said first and second ends, a threader which is semi-rigid, a tip on one end and a trailing end on another, a length (L') in between and a curvature formed substantially along the length (L'), said trailing end being integrally attached to, and bonded to, said strand at least one of said first end and second end, and a quick release section for interconnecting adjacent ones of said dental floss sections.

It is yet another feature of the present invention to provide a dispensable dental floss, comprising a plurality of interconnected dental floss sections each including a strand having a first end and a second end, a diameter (D), and a length (L) in between said first end and second end, a threader having a tip, a trailing end, a length (L') and a curvature formed substantially along the length (L'), said trailing end being integrally attached to, and integrally bonded to, said strand at least one of said first end and second end, and a quick release section interconnecting said threader of one dental floss section to one of an adjacent threader of an adjacent dental floss section and an end of said strand of an adjacent dental floss section, a spool upon which said plurality of interconnected dental floss sections are wound, and a dispenser into ,which said spool is inserted, said spool being free to rotate within said dispenser for dispensing said interconnected dental floss sections.

It is an advantage of the present invention that the floss can be easily removed from the dispenser without the user having to cut the floss and that a separate floss threading step is no longer required.

It is a further advantage that the floss can be manufactured in production quantities at a low cost.

It is an advantage of the present invention that the floss can be easily threaded through the user's teeth and underneath braces and bridgework with relative ease because the threader exhibits sufficient rigidity.

It is an advantage of the present invention that the floss can be easily grasped by the user from inside the mouth and the preferred curvature keeps the threader from contacting the roof of the mouth, properly positions the threader in the mouth for ease of grasping, and allows easier threading between the user's back teeth.

Additional inventive features will become apparent after viewing the attached drawings and reading the accompanying detailed description.

BRIEF DESCRIPTION OF THE DRAWINGS

FIG. 1 is an isometric view of a "prior art" dental floss in a dispenser box;

FIG. 2A is a frontal view of a "prior art" dental floss device;

FIG. 2B is a frontal view of a "prior art" dental floss threader;

FIG. 2C is an isometric view of a "prior art" dental floss including a spongy section;

FIG. 2D is a frontal view of a brace wearer's teeth;

FIG. 2E is an isometric view of a person's bridgework;

FIG. 3A is a sectioned side view of the present invention dental floss for brace wearers and the like;

FIG. 3B is an isometric view of the dental floss for brace wearers and the like being dispensed from a flip-top dispenser;

FIG. 3C is a side sectional view of the dental floss showing a quick release section connecting one section of floss to another section of floss in a tip-to-tip configuration;

FIG. 3D is a side sectional view of the dental floss along section line 3D;

FIG. 4 is a side sectional view of another embodiment of dental floss showing a quick release section connecting floss sections in a tip-to-end configuration;

DETAILED DESCRIPTION OF THE INVENTION

Figure 5:
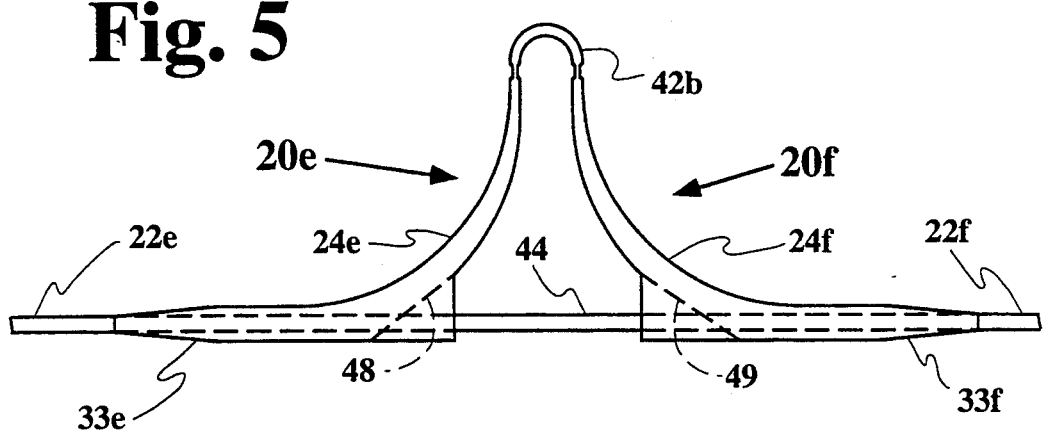
FIG. 5 is a side view of the dental floss quick release section shown in a tip-to-tip configuration and showing the cuts (dotted) to be made to remove the short strand section after the injection molding process.

In the following, the invention will be described in detail with respect to the preferred embodiments and the attached illustrations, and drawings. Referring now to FIG. 3A, is shown a side sectional view of the threadable dental floss 20. The floss 20 includes a strand 22 and a threader 24 which is integrally attached to, and bonded to, said strand 22. The threader 24 preferably includes a curvature formed along its length L' and is preferably of a radii of between 1.00 inch (in) and 2.00 inch (in) and ideally about 1.5 inch (in) which extends from the tip 30 to the trailing end 32. A taper 33 ensures that there is a smooth transition to the diameter of the strand 22. This preferable curvature enables the user to easily insert the threader 24 between back-most molars. It also allows the user to have something substantial to grasp when the threader 22 is inserted into the mouth cavity. Furthermore, the curvature keeps the threader 22 away from the roof of the mouth and properly positioned in the center of the mouth so that it is easier to grasp by the user. By the term integrally bonded, it is desired to have a molecular bond between the strand 22 material and the plastic material used to form the threader 24.

The strand 22 is preferably made of a dental floss material such as multiple-ply acrylic fibers, cotton, wool, or the like. The strand 22 is preferably manufactured from a plurality of strands which are slightly interwoven such that they keep their form and which are approximately 0.006 inch (in) in diameter. The strand 22 includes a length L, a diameter D, a first end 26, and a second end 26'. In this embodiment, the threaders 24 and 24'are bonded to either end of the strand 22. In this configuration, the floss 20 was bonded in what is referred to as a tip-to-tip relationship. The floss 20 could be cut midriff (half way between the threaders 24 and 24') to split the floss 20 into two usable sections if desired. However, if the user is in a hurry, the floss section 20 need not be cut at all. The user only needs to strip off one section including threaders 24 and 24' and use either end for threading the floss 20. In this manner, the threaders 24 and 24' act as mini-handles to keep the floss from slipping through the user's hands.

The threader 22 preferably has a cross section that is round, although a square, oblong, rectangular cross section, or the like, would be acceptable as well. The threader 24 includes a tip 30 and a trailing end 32 and is manufactured from preferably a semi-rigid thermoplastic material. The material is preferably semi-rigid, i.e., rigid enough to provide a convenient threader mechanism, yet is flexible or compliant enough not to shatter if flexed too much. Further, the material should have the ability to neck down under tensile loads such that the material exhibits a ductile break, i.e., the break is blunt and dull and not sharp edged. Preferable materials might include polyethylene, nylon, acetal homopolymer or copolymer, or the like. The ideal material should preferably have a low friction coefficient to easily slip through between the interproximal spaces between the user's teeth.

In FIG. 3B, the dispensable dental floss 20 is shown being dispensed from a flip top container 34. The floss 20 is unwound from an internal spool (not shown) as the user pulls on the threader 24 or strand 22. The container 34 includes a hollow body 36 and a flip-top 38 and a latch 40. A cutter 42 can be attached to the body 36, flip-top 38, or elsewhere to aid in cutting the strand 22 in between the ends 24 and 24' (FIG. 3A), although this is optional. All the user needs to do is to pull with a small force on the floss section 20 while holding the adjacent attached floss section (with thumb or otherwise). The floss 20 will release via a quick release section in between the adjacent sections of floss and is ready for use.

FIG. 3C illustrates two threadable sections of floss 20a, 20b arranged in a tip-to-tip configuration or relationship. Each floss 20a, 20b includes a strand 22a, 22b including first end 26a, 26b and a second end (not shown) and threader 24a, 24b. A quick release section 42 connects or interconnects the tips 30a and 30b of each of threaders 24a and 24b. This quick release section 42 provides a means for quickly disconnecting, breaking, or loosening one section of floss 20a from the other section of floss 20b. The section 42 is arranged so that the user can exert a small amount of force (approximately 2 pounds (1b) or less) and the two sections of floss 20A, 20B will separate. The material used for the threaders 24a, 24b is pliable enough not to shatter, but necks down and cleanly breaks leaving a blunt point which is not harmful or sharp to the user. The quick release section is made as small as required to allow the section to be easily removed.

FIG. 3D illustrates a sectional side view of floss 20 illustrating that the thickness (t) of threader 24 is not substantially thicker than the diameter (d) of the strand 22. This allows the threader 24 to easily be inserted between the teeth. The preferable diameter is between the range of 0.008 inches (in) and 0.0016 inches (in) and is preferably about 0.012 inches (in).

FIG. 4 illustrates another configuration of interconnecting floss sections 20c and 20d. The threader 24e is connected through a quick release section 42a to the second end 28d of strand 22d. This section 42a is intentionally necked down such that a clean break at that section 42A is assured.

FIG. 5 illustrates another configuration of interconnecting floss sections 20e and 20f. During the injection molding process, the threaders 24e and 24f are integrally bonded to the cord. This forms an integral bond between the strands 22e and threader 24e and the strand 22f and the threader 24f. During the process, the short section of cord 44 is removed by making cuts along lines 48 and 49 (shown dotted). This operation is formed with a hot knife or the like such that a clean cut is formed. During the injection molding process, the quick release section 42b is also formed which can be easily snapped off by the user to disconnect the sections of floss 20e and 20f. The quick release section includes at least one necked down section to ensure release at the necked down point.

Figure 6:
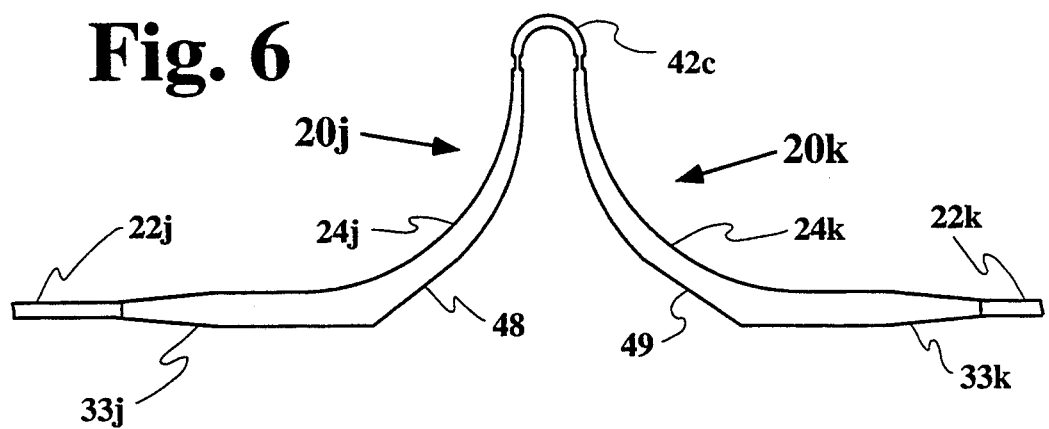
FIG. 6 is a side view of the dental floss quick release section shown in a tip-to-tip configuration and showing the short strand section removed.

FIG. 6 illustrates interconnecting floss sections 20j and 20k with the short section 44 (FIG. 5) having been removed. After the short section 44 (FIG. 5) is removed, the interconnected sections of floss such as 20j and 20k can be wound onto a spool (not shown). Because quick release section 42e is pliable, the threaders 20j and 20k can conform to the contours of the spool.

Figure 7:
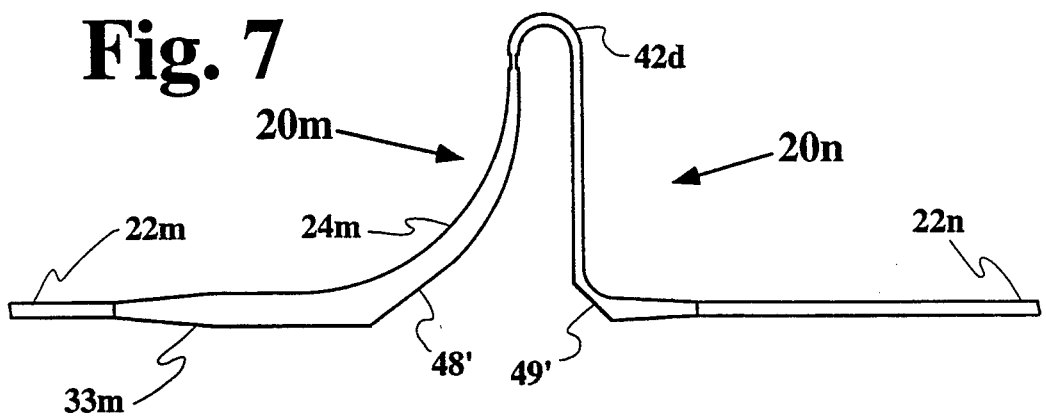
FIG. 7 is a side view of the dental floss showing another quick release section and shown in tip-to-end configuration.

FIG. 7 illustrates interconnecting floss sections 20m and 20n. These sections are attached in a tip-to-end configuration. Quick release section 42d is removed by breaking the necked down connection attached at threader 24m and then snapping off the remaining section of section 42d from strand 22n. The short section (not shown) is removed by making cuts 48' and 49' similar to cuts 48 and 49 of FIG. 5. This allows the sections of floss 20m and 20n to be attached and interconnected only at the quick release section 42d.

Figure 8:
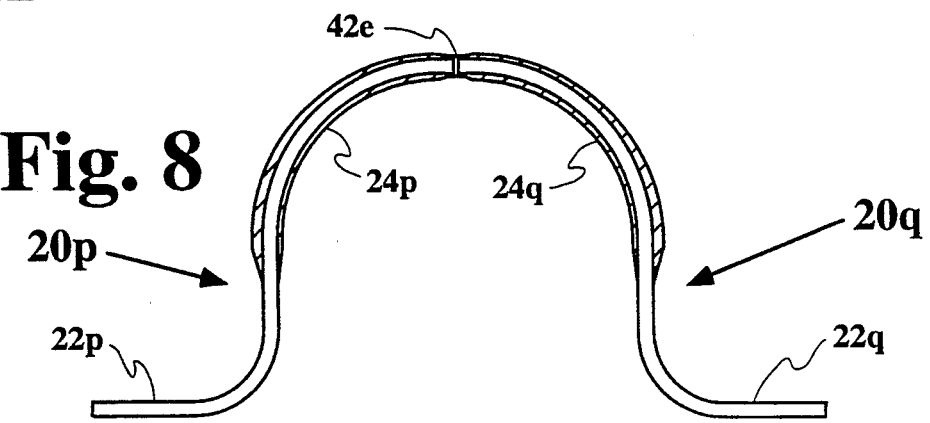
FIG. 8 is a side sectional view of the dental floss showing another quick release section in end-to-end configuration.

FIG. 8 illustrates another embodiment of interconnected floss sections 20p and 20q. In this embodiment, the strands 22p and 22q are encased within the threaders 24p and 24q. The strand is cut prior to injection molding adjacent quick release section 42e. The combination of necking down section 42e and the cut in the cord will induce the break at the quick release section 42e.

Figure 9:
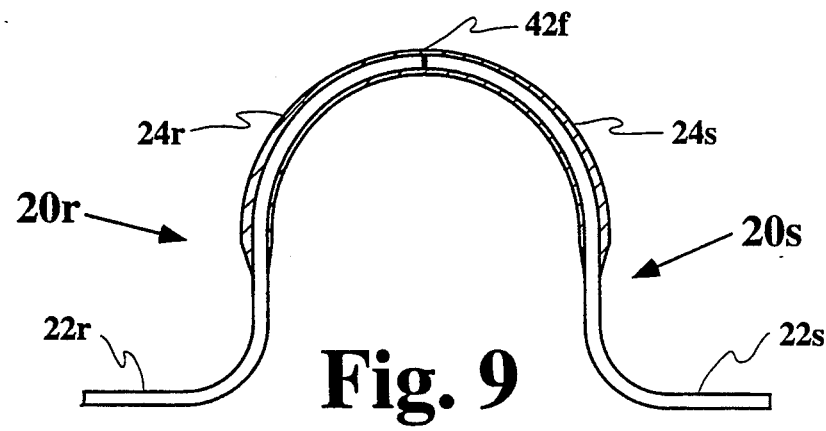
FIG. 9 is a sectional side view of the dental floss showing another quick release section in end-to-end configuration.

FIG. 9 illustrates interconnecting floss sections 20r and 20s. This embodiment is substantially similar to the embodiment of FIG. 8 except that the quick release section 42f does not include a necked down section. The cut alone causes the break at the quick release section 42f by causing a stress concentration at that point.

Figure 10:
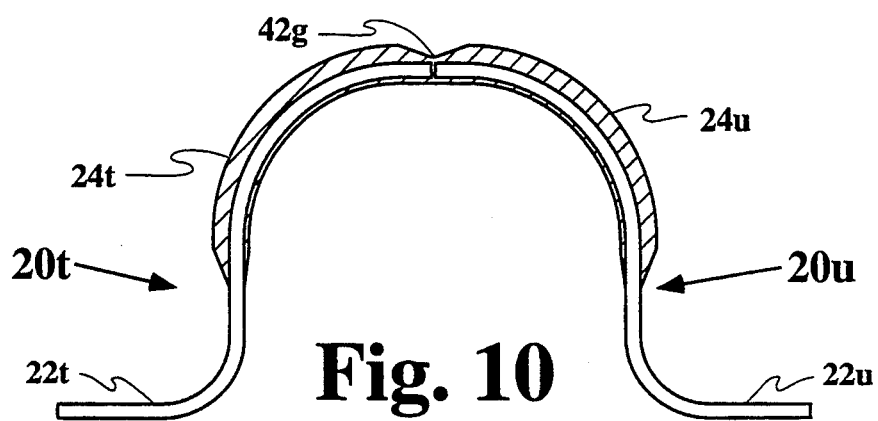
FIG. 10 is a sectional side view of the dental floss showing another quick release section in end-to-end configuration.

FIG. 10 illustrates interconnecting floss sections 20l and 20u. This embodiment is substantially similar to the embodiment of FIG. 8 except that the cross section is not circular. The cross section is rectangular and adds rigidity.

Figure 11:
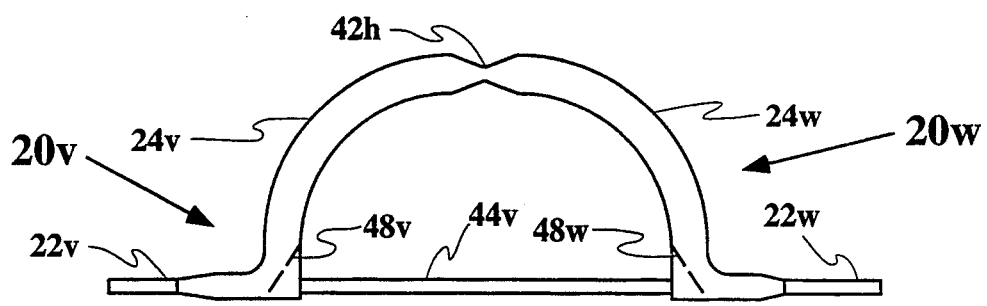
FIG. 11 is a side view of the dental floss showing another quick release section in end-to-end configuration.

FIG. 11 illustrates interconnecting floss sections 20v and 20w. This embodiment is substantially similar to the embodiment of FIG. 5 except that the radii on the threaders 24v and 24w face each other rather than being opposed. The cross section can be either round, square or rectangular. Section 44v is removed after injection molding by making cuts along lines 48v and 48w.

Figure 12:
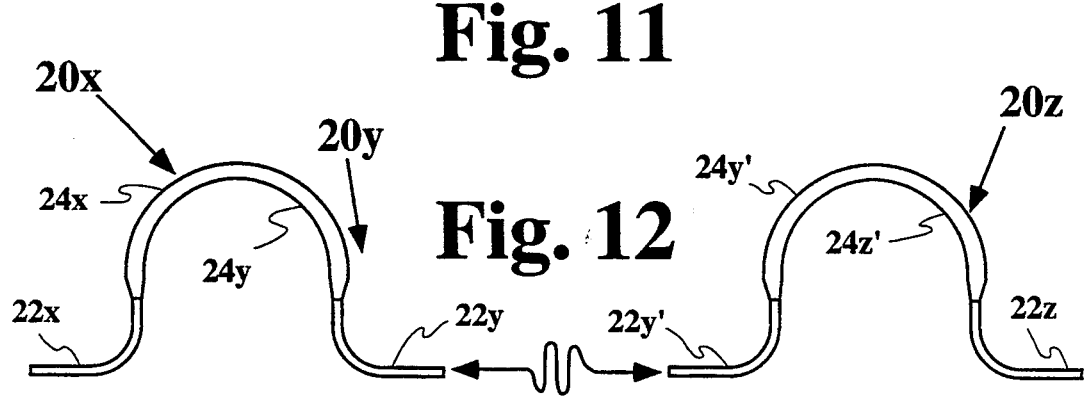
FIG. 12 is a side view of the dental floss showing multiple quick release sections in end-to-end configuration within a chain of floss.

FIG. 12 illustrates interconnecting floss sections 20x, 20y and 20z interconnected in a chain-like fashion. This embodiment illustrates the configuration of FIG. 9 attached in a chain. The sections of usable floss 20x, 20y and 20z are interconnected as removed from the injection process and then wound onto a spool. The radii of the curvatures on the threaders 24x, 24y, 24y', and 24z may be preferably substantially matched to the radii on the dispensing spool.

Figure 12A:
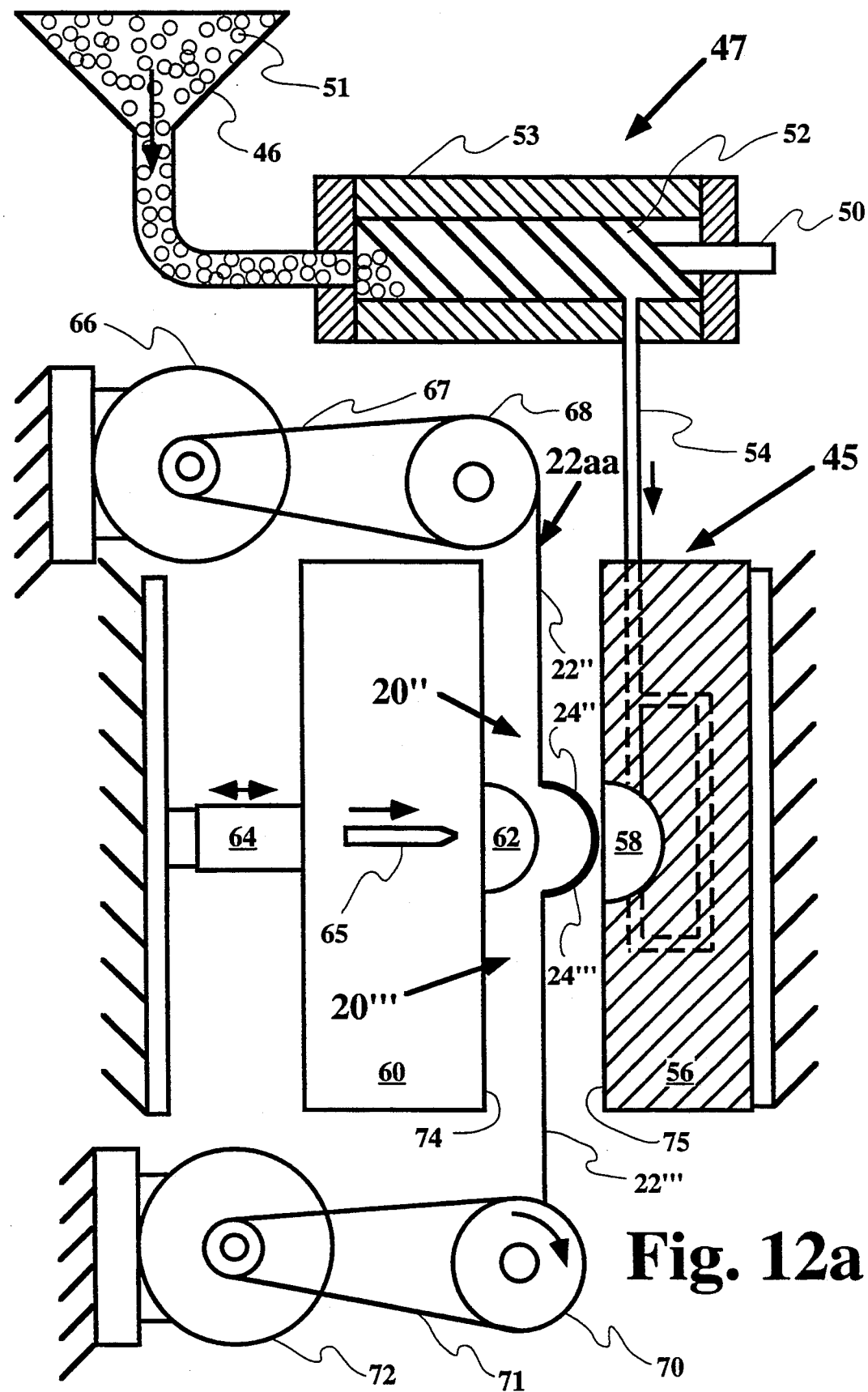
FIG. 12a is a view of the apparatus for forming chains of dental floss including quick release sections.

FIG. 12a illustrates an apparatus and process for forming the chain-like interconnected sections of floss 20″ and 20‴ which are useful for flossing the teeth of brace wearers and the like. The floss sections 20″ and 20‴ are formed during an injection molding process utilizing an injection mold 45. The process includes adding the appropriate starting plastic material 51 in pellet or bead form into a hopper 46. The material 51 is heated and extruded in screw 47. The screw 47 includes a case 53, an extruder blade 52, and a shaft 50 which is driven by motor (not shown). The plastic material 51 upon being heated into a molten and flowing state is then injected through feed line 54 into first and stationary mold half 56.

The proper sequence for forming the floss sections 20″ and 20‴ is to open the mold 45, pulling at least one strand 22aa from the spool of strand material 68 through the mold 45 and tying off on receiving rotatable spool 70. Spools 68 and 70 are driven by motors 66 and 72 via belts 67 and 71 such that the proper tension is maintained on at least one strand 22aa during the process. The mold 45 is then closed such that the at least one strand 22aa passes through the mold cavity in said mold 45. The mold cavity is formed by recess 58 in first mold half 56 and projection 62 on second mold half 60. Upon closing the mold 45 via actuation of actuator 64, the at least one strand 22aa rides over projection 62 and is bent off of a straight-line course into the proximity of the recess 58. The design of the mold is such that the appropriate mold cutoff is achieved on at least one strand 22aa. Once the mold 45 is closed, a cutting member 65 is inserted into the mold cavity to cut strand 22aa adjacent to the area where threaders 24″ and 24‴ will be injected molded. The cut is precisely located where the quick release section, for example 42e (FIG. 8), will be. The cutting member 65 is retracted and the injection molding is accomplished by injecting molten plastic material 51 into the mold cavity. After a short cure cycle, the mold 45 is opened and the interconnected floss sections 20″ and 20‴ are wound onto the spool 70. The spools 68 and 70 can either be the end-user dispensing spool or a large spool from which the user-ready spools are wound from.

Alternatively, the configurations of FIGS. 6, 7 and 11 where there is a short section to be removed after injection molding can be formed using a similar process. The difference being is that the cut is made after the injection molding. Furthermore, there is no need for the projection 62 as the molding can take place in the plane of the faces 74 and 75 of the mold halves 56 and 60. The cut to remove the short section may be accomplished prior to or after winding onto spool 70. Depending on the process used, the threaders can be either tip-to-tip or tip-to-end configuration.

From the foregoing, it should be apparent that the present invention now provides a novel and inexpensive dental floss for persons who have braces, bridgework, and the like. While the preferred embodiment of the present invention has been described in detail, various modifications, alterations and changes may be made without departing from the spirit and scope of the present invention defined in the appended claims.

I claim:

1. A dental floss chain, comprising:
    (a) a plurality of interconnected dental floss sections, each adjacent dental floss section including;
        (i) a strand having a first end and a second end being formed by a cut severing completely therethrough, a diameter (D), and a length (L) in between said first and second ends,
        (ii) a threader which is formed of a semi-rigid material, having a tip on one end and a trailing end on another end, a length (L') in between, said trailing end being integrally attached to, and bonded to, said strand at at least one of said first end and second end, and
        (iii) a quick release section formed of said semi-rigid material for interconnecting said each adjacent dental floss section, said quick release section being formed directly adjacent said cut and including a complete separation of said strands,
    whereby each said adjacent dental floss section is separated from one another by a user exerting a small force and without a cutting operation.

2. A dental floss chain of claim 1 wherein said threader is round in cross section and has a diameter in the range of between 0.008 inch and 0.016 inch.

3. A dental floss chain of claim 1 wherein said threader is manufactured from a plastic material and is integrally bonded to, and attached to, said strand by an injection molding process.

4. A dental floss chain of claim 1 wherein said end is formed by said cut formed directly adjacent to said tip on said threader prior to bonding.

5. A dental floss of claim 1 wherein said plurality of interconnected dental floss sections are only interconnected by said quick release section because an interconnecting short portion of said strand has been removed.

6. A dental floss chain of claim 1 wherein said threader includes a curvature substantially along said length (L').

7. A dental floss chain of claim 1 wherein said plurality of interconnected dental floss sections are interconnected by said quick release section which attaches between one of said first end and said second end of said strand and said threader on said adjacent floss section.

8. A dental floss chain of claim 1 wherein said plurality of interconnected dental floss sections are interconnected by said quick release section which attaches threaders from adjacent dental floss sections in tip-to-tip relationship.

9. A dispensable dental floss, comprising:

(a) a plurality of interconnected dental floss sections, each adjacent dental floss section including;
  (i) a strand having a first end and a second end being formed by a cut severing completely therethrough, a diameter (D), and a length (L) in between said first end and second end,
  (ii) a threader being manufactured from a semi-rigid material by injection molding having a tip, a trailing end, a length (L') and a curvature formed substantially along the length (L'), a round cross section, said trailing end being integrally attached to, and integrally bonded to, said strand at at least one of said first end and second end, and
  (iii) a quick release section interconnecting said threader of one dental floss section to one of an adjacent threader of said adjacent dental floss section and said end of said strand of said adjacent dental floss section and including a complete separation of said strands;
(b) a spool upon which said plurality of interconnected dental floss sections are wound; and
(c) a dispenser into which said spool is inserted, said spool being free to rotate within said dispenser for dispensing said interconnected dental floss sections; and whereby said adjacent dental floss sections are separated from one another by a user exerting a small force and without a cutting operation.

10. A dental floss of claim 9 wherein said quick release section is separable by exerting a force of about two pounds.

11. A dental floss of claim 9 wherein said threader is manufactured from a plastic material and is integrally bonded and attached to said strand by an injection molding process.

12. A dental floss of claim 9 wherein said strand is manufactured from acrylic fiber and said threader is manufactured from a plastic material.

13. A dental floss of claim 9 wherein said plurality of interconnected dental floss sections are interconnected by said quick release section which attaches between a threader of one dental floss section and a threader on an adjacent floss section, said quick release section including a complete separation of said strands of said plurality of interconnected dental floss sections.

14. A dental floss of claim 9 wherein means for allowing the plurality of interconnected dental floss sections to be removed from said dispenser include a flip top on said dispenser and a cutting edge for cutting said dental floss sections into two usable sections in-between said ends of said strand.

15. A dental floss of claim 9 manufactured by the process steps of:
  (a) opening an injection mold having at least one mold cavity;
  (b) pulling at least one strand through said mold and connecting said at least one strand to at least one rotatable spool;
  (c) closing said mold such that said at least one strand is situated in said mold to provide cutoff for said at least one strand and that said at least one strand passes through said at least one mold cavity;
  (d) molding at least one threader onto said at least one strand in a configuration selected from the group consisting of tip-to-tip relationship and tip-to-end relationship and thus forming an integral bond between said at least one threader and said at least one strand and forming a quick release section;
  (e) opening said mold;
  (f) cutting a short section of said strand such that said plurality of interconnected dental floss sections are interconnected only by said quick release section;
  (g) winding said at least one strand and interconnected threaders ahead onto said spool; and
  (h) repeating steps (c) through (g) until said spools are ready for removal.

16. A dental floss of claim 9 manufactured by the process steps of:
  (a) opening an injection mold having at least one mold cavity;
  (b) pulling at least one strand through said mold and connecting said at least one strand to at least one rotatable spool;
  (c) closing said mold such that said at least one strand is situated in said mold to provide cutoff for said at least one strand and that said at least one strand passes through said at least one mold cavity;
  (d) cutting said at least one strand in an area where said at least one strand passes through said mold cavity;
  (e) molding at least one threader onto said at least one strand in a configuration selected from the group consisting of tip-to-tip relationship and tip-to-end relationship and thus forming an integral bond between said at least one threader and said at least one strand and forming a quick release section;
  (f) opening said mold;
  (g) winding said at least one strand and interconnected threaders ahead onto said spool; and
  (h) repeating steps (c) through (g) until said spools are ready for removal.

17. A process of manufacturing a dental floss chain, comprising the steps of:
  (a) opening an injection mold having at least one mold cavity;
  (b) pulling at least one strand through said mold;
  (c) closing said mold such that said at least one strand is situated in said mold to provide cutoff for said at least one strand and that said at least one strand passes through said at least one mold cavity;
  (d) cutting completely through said at least one strand in an area where said at least one strand passes through said mold cavity;
  (e) molding a quick release section onto said at least one strand in a configuration consisting of tip-to-tip relationship and tip-to-end relationship and thus forming an integral bond between said at least one threader and said at least one strand; and
  (f) opening said mold and removing said dental floss chain.

18. A process of manufacturing a dental floss chain of claim 17 further including the step of winding said dental floss chain onto a rotable spool.

19. A process of manufacturing a dental floss chain of claim 18 further including the step of inserting said rotable spool into a dispenser.

* * * * *

UNITED STATES PATENT AND TRADEMARK OFFICE
CERTIFICATE OF CORRECTION

PATENT NO. : 5,392,794
DATED : February 23, 1995
INVENTOR(S) : John P. Striebel

BEST AVAILABLE COPY

It is certified that error appears in the above-indentified patent and that said Letters Patent is hereby corrected as shown below:

On the title page item [76],

Change "John S. Striebel" to --John P. Striebel--

Signed and Sealed this

Sixth Day of June, 1995

BRUCE LEHMAN

Attest:

Attesting Officer    Commissioner of Patents and Trademarks